US009011370B2

(12) United States Patent
Abal

(10) Patent No.: US 9,011,370 B2
(45) Date of Patent: Apr. 21, 2015

(54) DEFORMABLE VALVE MECHANISM FOR CONTROLLING FLUID DELIVERY

(75) Inventor: Daniel Abal, San Diego, CA (US)

(73) Assignee: Carefusion 303, Inc., San Diego, CA (US)

( * ) Notice: Subject to any disclaimer, the term of this patent is extended or adjusted under 35 U.S.C. 154(b) by 614 days.

(21) Appl. No.: 12/779,758

(22) Filed: May 13, 2010

(65) Prior Publication Data

US 2011/0282276 A1 Nov. 17, 2011

(51) Int. Cl.

| | |
|---|---|
| ***A61M 1/00*** | (2006.01) |
| ***A61M 5/00*** | (2006.01) |
| ***F16K 1/00*** | (2006.01) |
| ***F16K 15/00*** | (2006.01) |
| ***F16K 1/38*** | (2006.01) |
| ***A61M 5/142*** | (2006.01) |
| ***A61M 39/22*** | (2006.01) |
| ***F16K 7/12*** | (2006.01) |
| ***F16K 7/16*** | (2006.01) |
| *A61M 5/168* | (2006.01) |

(52) U.S. Cl.

CPC .............. *F16K 1/38* (2013.01); *A61M 5/14212* (2013.01); *A61M 5/16827* (2013.01); *A61M 39/22* (2013.01); *A61M 2039/226* (2013.01); *A61M 2205/0216* (2013.01); *A61M 2205/128* (2013.01); *F16K 7/12* (2013.01); *F16K 7/16* (2013.01)

(58) Field of Classification Search

USPC .......... 604/246–256, 33; 251/12, 14, 84, 213, 251/334

See application file for complete search history.

(56) References Cited

U.S. PATENT DOCUMENTS

| | | | | |
|---|---|---|---|---|
| 2,638,127 | A | 5/1953 | Griswold | |
| 3,011,758 | A * | 12/1961 | McFarland, Jr. | 251/331 |
| 3,802,462 | A * | 4/1974 | Trosch | 137/556 |
| 4,072,292 | A * | 2/1978 | Banon | 251/331 |
| 4,300,552 | A * | 11/1981 | Cannon | 604/65 |
| 4,375,882 | A * | 3/1983 | Schreiber, Jr. | 251/266 |
| 4,415,003 | A | 11/1983 | Paradis et al. | |
| 4,515,588 | A | 5/1985 | Amendolia | |
| 4,537,387 | A * | 8/1985 | Danby et al. | 251/331 |
| 4,561,428 | A * | 12/1985 | Konomura | 604/119 |
| 4,703,775 | A * | 11/1987 | Pastrone | 604/33 |
| 4,769,012 | A | 9/1988 | Quang et al. | |
| 4,925,451 | A | 5/1990 | Amendolia | |
| 5,249,600 | A | 10/1993 | Blume | |
| 5,520,661 | A | 5/1996 | Lal et al. | |
| 6,123,320 | A * | 9/2000 | Rasanow et al. | 251/331 |

(Continued)

FOREIGN PATENT DOCUMENTS

| | | |
|---|---|---|
| CA | 2171729 | 1/2006 |
| EP | 1099455 | 5/2001 |

(Continued)

*Primary Examiner* — Matthew F Desanto

(74) *Attorney, Agent, or Firm* — McDermott Will & Emery LLP

(57) ABSTRACT

A valve for controlling delivery of fluid includes a valve seat comprising a fluid inlet, a fluid outlet and a conical well having an opening, a beveled surface and a bottom, and a valve membrane comprising a conical portion having a base and a tip. The conical portion is configured to fit within the conical well of the valve seat. The valve membrane is configured to fluidly connect the fluid inlet to the fluid outlet when the valve membrane is in an undeformed position and fluidly disconnect the fluid inlet from the fluid outlet when the valve membrane is in a radially deformed position.

12 Claims, 7 Drawing Sheets

(56) References Cited

U.S. PATENT DOCUMENTS

| | | | | |
|---|---|---|---|---|
| 6,390,130 | B1 | 5/2002 | Guala | |
| 6,416,038 | B1 * | 7/2002 | Sindel et al. | 251/331 |
| 6,497,680 | B1 * | 12/2002 | Holst et al. | 604/153 |
| 6,648,006 | B1 * | 11/2003 | Ostergaard | 251/331 |
| 6,796,515 | B2 | 9/2004 | Heren et al. | |
| 7,232,423 | B2 * | 6/2007 | Mernoe | 604/135 |
| 7,389,788 | B2 | 6/2008 | Wilson et al. | |
| 2002/0004015 | A1 * | 1/2002 | Carlisle et al. | 417/479 |
| 2009/0062738 | A1 | 3/2009 | Ziegler | |
| 2009/0072173 | A1 * | 3/2009 | Hasunuma et al. | 251/129.12 |

FOREIGN PATENT DOCUMENTS

| | | |
|---|---|---|
| GB | 2167161 | 5/1986 |
| NL | 8205083 | 12/1983 |

* cited by examiner

DEFORMABLE VALVE MECHANISM FOR CONTROLLING FLUID DELIVERY

FIELD

The present disclosure relates to delivery of fluids. Specifically, the present disclosure relates to a valve mechanism for controlling delivery of medical fluids.

BACKGROUND

A valve mechanism is the primary control element that controls the direction and volume of fluid flow in an intravenous (IV) infusion pump. Most valves operate through the application of an actuation force and a restorative force provided, for example, by a pump mechanism on a durable portion, to open and close a fluid pathway. Generally, a pump mechanism includes an actuation feature (e.g., mechanical "fingers") that extends out to the valve located on a disposable portion. The actuation feature is used to pinch together two surfaces in a fluid path to close the valve. The actuation feature is retracted back to open the valve. For proper operation including complete closure of the fluid path, the actuation feature needs to be designed and built to a tight tolerance specification.

Tight tolerances on the design of a valve and an actuation feature generally increase the manufacturing cost of disposable and durable portions of an IV infusion pump. Therefore, it is desirable to use a valve mechanism that is less sensitive to design and manufacturing tolerances.

SUMMARY

The above-discussed and other needs are addressed by an improved valve design.

In an aspect of the disclosure, a valve in a fluid delivery system is disclosed. The valve comprises a valve seat comprising a fluid inlet, a fluid outlet and a conical well having an opening, a beveled surface and a bottom. The valve also includes a valve membrane comprising a conical portion having a base and a tip. The conical portion is configured to fit within the conical well of the valve seat. The valve membrane is configured to fluidly connect the fluid inlet to the fluid outlet when in an undeformed position and fluidly disconnect the fluid inlet from the fluid outlet when in a radially deformed position.

In another aspect of the disclosure, a fluid delivery system for delivering fluid from a fluid source to a patient is disclosed. The fluid delivery system comprises a durable portion comprising an actuator mechanism and a disposable portion comprising a first valve fitted on the durable portion to allow the actuator mechanism to exert a pushing force on an actuation area of the first valve. The first valve is coupled to a first fluid inlet and a fluid outlet such that the first valve fluidly connects the first fluid inlet and the fluid outlet when the pushing force is not applied and deforms radially to fluidly disconnects the first fluid inlet from the fluid outlet when the pushing force is applied to the actuation area of the first valve.

In yet another aspect of the present disclosure, a valve for controlling delivery of fluid between a fluid inlet and a fluid outlet is disclosed. The valve comprises a first portion having a chamber fluidly connected to the fluid inlet and the fluid outlet. The valve further comprises a second portion having a protruding portion fitted within the chamber such that fluid can flow from the fluid inlet to the fluid outlet through the chamber around the protruding portion when the protruding portion is not deformed and fluid cannot flow from the fluid inlet to the fluid outlet through the chamber when the protruding portion is deformed to touch at least a portion of a wall of the chamber.

The foregoing and other features, aspects and advantages of the embodiments of the present disclosure will become more apparent from the following detailed description and accompanying drawings.

DETAILED DESCRIPTION

The disclosed embodiments address and solve problems related to the aforementioned deficiencies in valve designs. The embodiments solve these problems, at least in part, by providing a valve design that can operate without the need for a tightly controlled extension of a valve actuator. The disclosed embodiments further solve these problems, at least in part, by using a flexible material to provide a restorative force that opens a valve when an actuation force is removed. In one aspect, certain disclosed embodiments eliminate the need to have a retraction mechanism in a pump, thereby reducing the number of parts in a pump assembly by simplifying the valve actuation mechanism. By reducing the number of parts in a pump assembly, improved reliability and reduced cost can be achieved.

The earlier stated needs and others are met by still other disclosed embodiments that provide a valve in which a flexible valve membrane is configured to operate within a rigid valve seat to fluidly connect or disconnect a fluid inlet and a fluid outlet. When the valve membrane is in an undeformed position, fluid passes from the fluid inlet to the fluid outlet through a clearance between the valve membrane and a wall of the valve seat. Pushing against a portion of the valve membrane by an external force causes the valve membrane to deform in a radially outward direction, thereby closing the clearance between the valve membrane and the valve seat wall, and fluidly disconnecting the fluid inlet from the fluid outlet. When the external force is removed, the valve membrane resiles to the undeformed position, opening the clearance between the valve membrane and the valve seat wall, thereby once again allowing passage of fluid between the fluid inlet and the fluid outlet.

In certain embodiments, the valve membrane is shaped to have a flat portion with a hollow conical shape at the center of the flat portion. The hollow conical shape terminates with a cylindrical protrusion at the apex of the cone. The valve seat has a beveled surface that matches the conical shape of the valve membrane. When the valve membrane is in an undeformed position, a gap between a wall of the conical shape of the valve membrane and the beveled surface of the valve seat allows fluid to pass between the fluid inlet and the fluid outlet. When the valve membrane is caused to deform, the valve membrane radially deforms, thereby closing the gap between the conical shape and the beveled surface of the valve seat, resulting in fluidly disconnecting the fluid inlet from the fluid outlet.

According to certain embodiments, the flat portion of the valve membrane comprises a deformable portion that is accordion-pleated and has a hollow conical shape that terminates with a cylindrical protrusion at the apex of the cone. The accordion-like shape of the flat portion of the valve membrane advantageously helps radial deforming and resiling of the valve membrane.

Figure 1A:
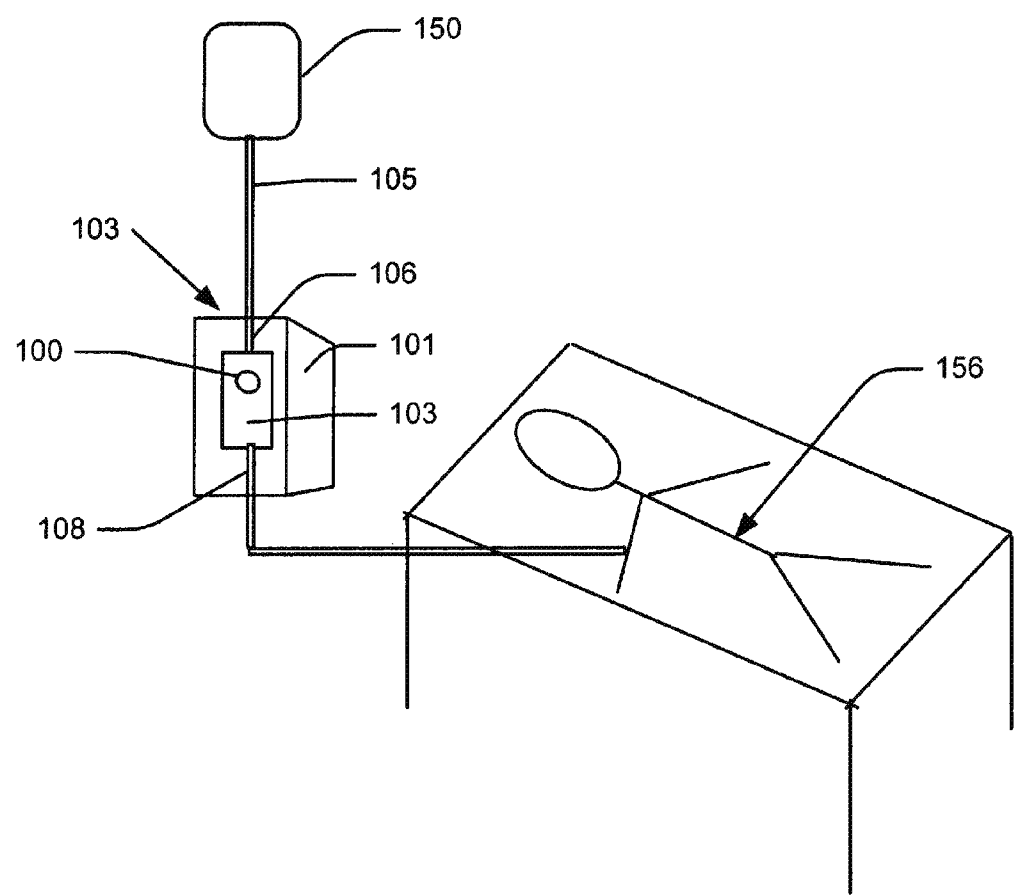
FIG. 1A is a diagrammatic view of a medical fluid delivery system, in accordance with embodiments of the present disclosure.

FIG. 1A illustrates a patient care system for delivery of fluid from fluid source 150 to patient 156 using fluid delivery system 103. Fluid delivery system 103 comprises durable portion 101 (e.g., a fluid pump) and disposable portion 103 (e.g., a disposable intravenous fluid delivery set) for delivering fluid from the fluid source 150 via the fluid line 105 to patient 156. Disposable portion 103 includes valve 100. In operation, an actuator mechanism (not shown in FIG. 1A) on durable portion 101 operates valve 100 to fluidly connect or disconnect fluid inlet 106 with fluid outlet 108 to control delivery of fluid to patient 156.

Figure 1B:
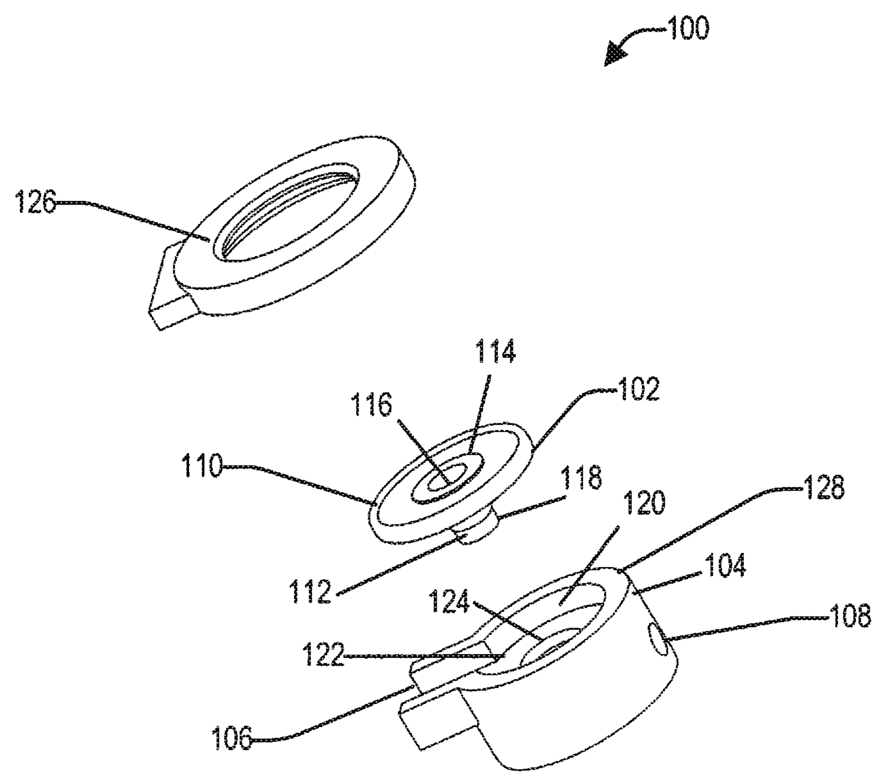
FIG. 1B is a diagrammatic view of a valve, in accordance with embodiments of the present disclosure.

FIG. 1B is an exploded perspective view of valve 100, in accordance with certain embodiments of the present disclosure. In the configuration illustrated in FIG. 1B, valve 100 comprises valve membrane 102 and valve seat 104. Valve seat 104 comprises two openings: fluid inlet 106 and fluid outlet 108. In certain embodiments, valve 100 may also comprise retaining cap 126. In certain aspects, retaining cap 126 is useful to securely hold valve membrane 102 in place during operation of valve 100. Retaining cap 126 is made of a rigid material, such as hard plastic, to ensure structural robustness of valve 100 and securely hold valve membrane 102 in place during operation to prevent unwanted fluid leakage from valve membrane 102.

Still referring to FIG. 1B, valve membrane 102 comprises flat portion 110 and conical portion 112. In the configuration illustrated in FIG. 1B, flat portion 110 is circular in shape. However, many other shape variations of flat portion 110 are possible. For example, in certain configurations, flat portion 110 may be oval. In certain configurations, when the oval portion has a major axis in the direction of a fluid channel and a minor axis along the width of a fluid channel, an oval flat portion 110 may provide a more streamlined fit of valve 100 within disposable portion 103 (not shown in FIG. 1B).

In the embodiment illustrated in FIG. 1B, conical portion 112 is at the center of flat portion 110. However, variations in placement of conical portion 112 with respect to flat portion 110 are possible consistent with configurations of the present disclosure. For example, in certain configurations, conical portion 112 may be placed off-center with respect to flat portion 110. In the configuration illustrated in FIG. 1B, conical portion 112 is depicted to have a circular cross-section. However, many other variations in cross-sectional shape of conical portion 112 are possible. For example, in certain embodiments, conical portion 112 may have an elliptical cross-section, e.g., to match an elliptical shape of flat portion 110. The cross-sectional shape of conical portion 112 may be selected to match the shape of an external actuator used to deform or resile valve membrane 102.

Still referring to FIG. 1B, conical portion 112 is hollow, having opening 116 at the base of conical portion 112. In certain aspects, the hollow nature of conical portion 112 provides deformability to valve membrane 102 to allow valve membrane 102 to deform in a radially outward direction when an external force is applied to region 114 (actuation area) of flat portion 110. Actuation area 114 is the region closest to opening 116 at the base of conical portion 112, and is provided for an external actuator to apply a pushing force towards conical portion 112 to cause conical portion 112 to deform in a radially outward direction, as further described below. Conical portion 112 conically protrudes from flat portion 110 and terminates in a cylindrical tip 118 at the apex of the cone. In certain configurations, valve membrane 102 is made of a resilient, elastomeric material such as silicone, so that valve membrane 102 stretches or deforms under application of an external force and resiles back to the original shape when the external force is removed.

Still referring to FIG. 1B, valve seat 104 comprises opening 120 on top side 128 of valve seat 104. Opening 120 is recessed and shaped to match the shape of flat portion 110. During operation, flat portion 110 of valve membrane 102 is securely fitted to form a fluid-tight contact with top side 128. Inner diameter of opening 120 is smaller than outer diameter of flat portion 110 so that when valve membrane 102 is fitted on top side 128 of valve seat 104, fluid can flow in space 238 (not visible in FIG. 1B) between flat portion 110 at the top and neck surface 122 of valve seat 104 at the bottom of the space. Neck surface 122 is recessed from top 126 of valve seat 104 at a depth smaller than the height of conical portion 112 so that when valve membrane 102 is fitted on top side 128 of valve seat 104, cylindrical tip 118 enters valve seat 104 through neck opening 124.

Figure 2:
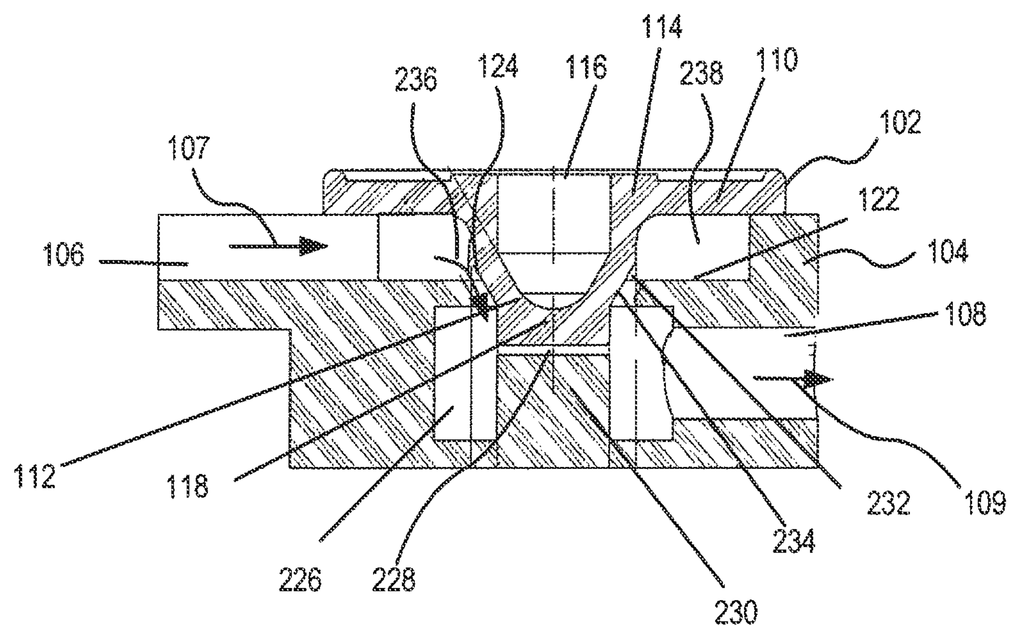
FIG. 2 is a diagrammatic cross-sectional view of a valve, in accordance with embodiments of the present disclosure.

FIG. 2 is a diagrammatic view of valve 100, in accordance with embodiments of the present disclosure. The view depicted in FIG. 2 shows a cross-sectional view of valve 100 when valve membrane 102 is in the undeformed position. In the undeformed position of valve membrane 102, fluid can flow, in the direction of arrow 107, from fluid inlet 106 to space 238. From space 238, fluid can flow through clearance 236 between beveled surface 234 of conical well 232 of valve seat 104 and conical portion 112 of valve membrane 102 (in the direction of arrow 113), to chamber 226 formed by a separation between conical portion 112 and valve seat 104. The fluid can continue to flow, in the direction of arrow 109, through chamber 226 and gap 228 between bottom 230 of conical well 232 and the tip of the conical portion 112 to fluid outlet 108. Therefore, fluid inlet 106 and fluid outlet 108 are fluidly connected when valve membrane 102 is in the undeformed position, as seen in FIG. 2. Conical well 232 has a beveled surface 234 matching shape of conical portion 112. In the undeformed position depicted in FIG. 2, conical tip 118 is shown positioned below neck opening 124.

Figure 3:
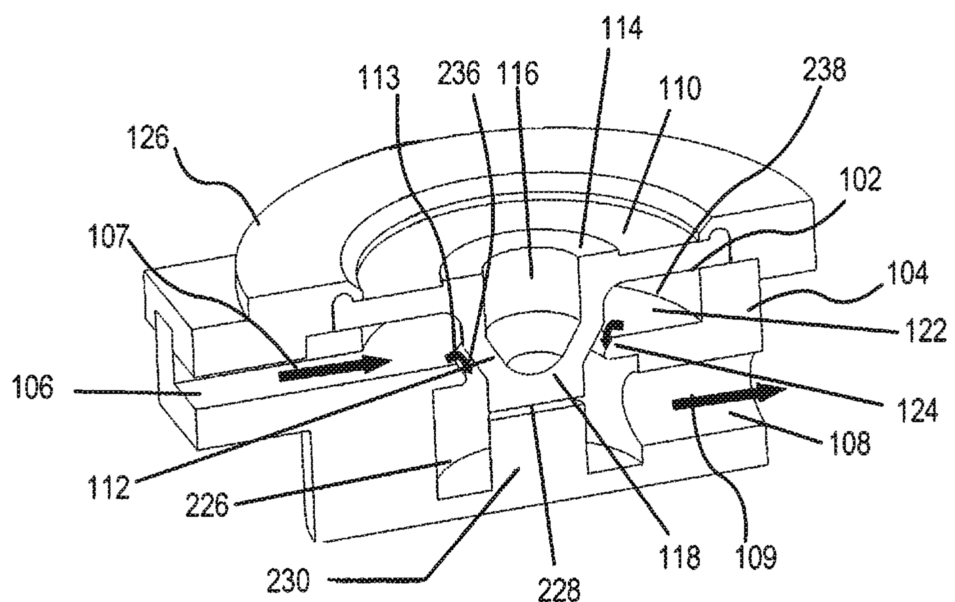
FIG. 3 is a diagrammatic cross-sectional view of a valve, in accordance with certain configurations of the present disclosure.

FIG. 3 is a diagrammatic view of valve 100, in accordance with certain configurations of the present disclosure. FIG. 3 depicts a three-dimensional perspective view of valve 100 cut in a plane passing through both fluid inlet 106 and fluid outlet 108. In certain configurations, fluid inlet 106 and fluid outlet 108 may be positioned at another angle than 180 degrees apart, around circumference of valve 100 (e.g., 90 degrees apart). In the view depicted in FIG. 3, valve membrane 102 is in the undeformed position and clearance 236, chamber 226 and gap 228 are visible. Clearance 236 may extend around the periphery of bottom 230. As described previously, fluid entering fluid inlet 106 travels in the direction of arrow 107, into space 238. The fluid then flows to chamber 226 through clearance 236, in the direction of arrow 113. The fluid also flows through gap 228. The fluid then flows from chamber 226 to fluid outlet 108, in the direction of arrow 109.

Figure 4:
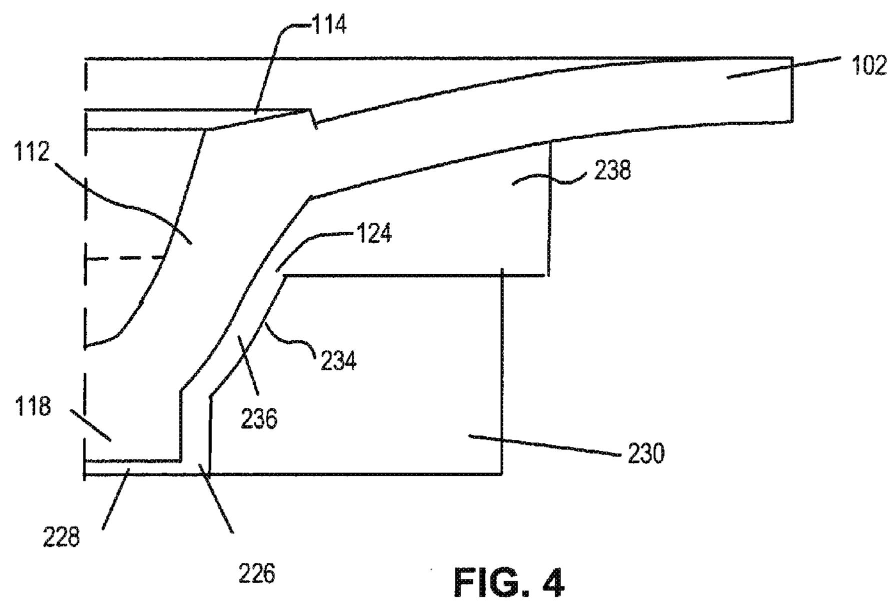
FIG. 4 is a diagrammatic cross-sectional view of a portion of a valve, in accordance with certain configurations of the present disclosure.

FIG. 4 is a diagrammatic view of a portion of valve 100, in accordance with certain embodiments of the present disclosure. The portion of valve 100 depicted in FIG. 4 includes clearance 236 between beveled surface 234 and conical portion 112. FIG. 4 depicts valve membrane 102 and conical portion 112 in an undeformed position. In the deformed position of conical portion 112, clearance 236 is present between beveled surface 234 and conical portion 112. Clearance 236 allows fluid to flow between space 238 and chamber 226. In the embodiment depicted in FIG. 4, only the portion of chamber 226 between gap 228 and neck opening 124, including the portion of chamber around cylindrical tip 118, is visible.

Figure 5:
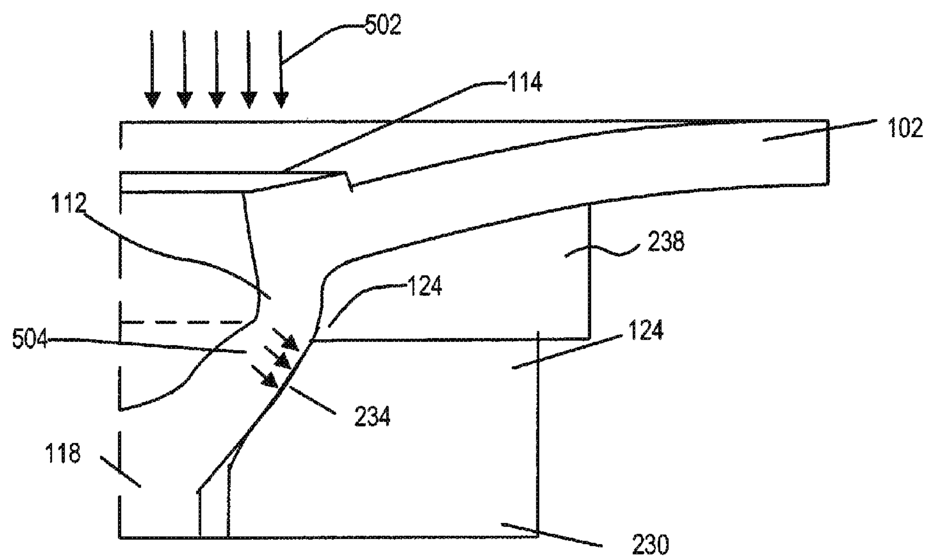
FIG. 5 is a diagrammatic cross-sectional view of a portion of a valve, in accordance with certain configurations of the present disclosure.

FIG. 5 is a diagrammatic view of a portion of valve 100, in accordance with certain embodiments of the present disclosure. FIGS. 4 and 5 depict the same portion of valve 100. In contrast to the configuration depicted in FIG. 4 in which valve membrane 102 is in undeformed position, FIG. 5 depicts valve membrane 102 radially deformed by an external force (indicated by arrows 502) applied to actuation area 114 of valve membrane 102 in the direction of conical portion 112. In certain embodiments, application of force 502 may initially push conical portion 112 downwards (in the direction of force 502) thereby first closing gap 228 (not shown in FIG. 5) between cylindrical tip 118 and bottom 230 (not shown in FIG. 5). Continued application of force 502 then results in radial deformation (or stretching) of conical portion 112 into clearance 236 between conical portion 112 and beveled surface 234 (in the direction of arrows 504), causing the closing off of clearance 236. Because of the closure of clearance 236, now there is no fluid contact between space 238 and chamber 226. Therefore, fluid inlet 106 is now fluidly disconnected from fluid outlet 108. Thus, by using an external force 502 (e.g., using actuators located on durable portion 101), valve 100 can be operated to prevent fluid delivery between fluid inlet 106 and fluid outlet 108. In certain embodiments, valve membrane 102 and conical portion 112 are made from an elastomeric material (i.e., capable of elastically deforming under force), thereby causing conical portion 112 to deform and radially stretch under external force 502, thereby closing off valve 100.

Still referring to FIG. 5, when external force 502 is removed from actuation area 114, resiliency of valve membrane 102 causes valve membrane 102 to resile back to the undeformed position (e.g., as depicted in FIG. 3). In other words, the energy required to restore the “open” position of valve 100 is stored in the valve membrane 102 in radially deformed position. This restoring energy is then released, when external force 502 is removed, causing valve membrane 102 to restore to the undeformed position. As discussed previously, when valve membrane 102 is in the undeformed position, fluid can flow between fluid inlet 106 and fluid outlet 108. Therefore, by applying and removing an external pushing force, valve 100 can be operated to turn off or on a fluid flow through valve 100.

Figure 6:
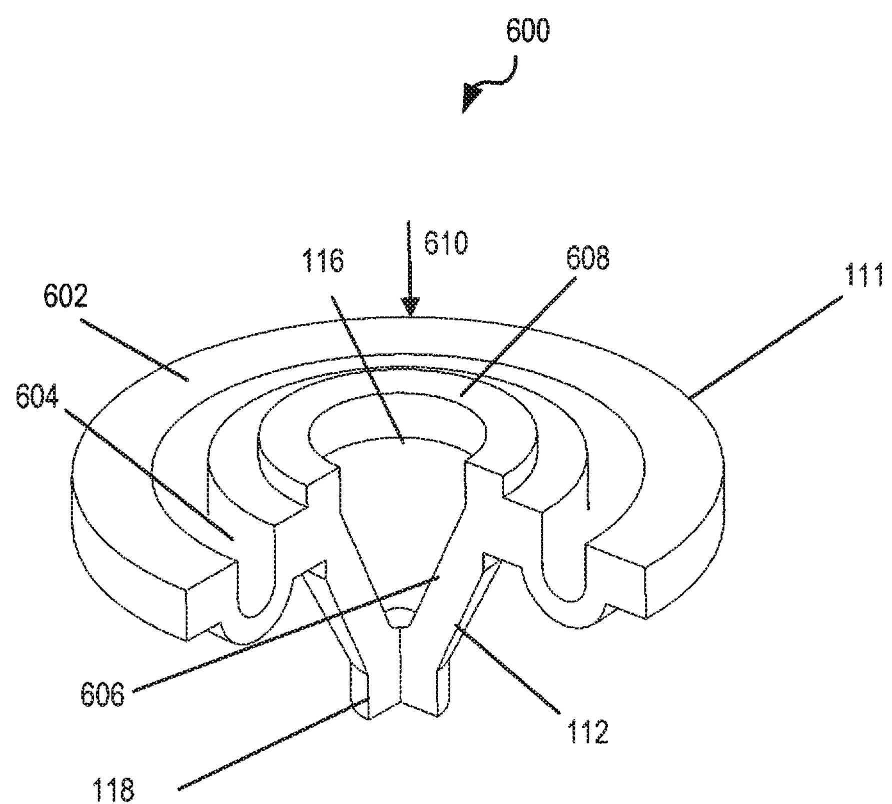
FIG. 6 is a diagrammatic view of a valve membrane, in accordance with certain configurations of the present disclosure.

FIG. 6 is a perspective and partial sectioned view of valve membrane 600 in accordance with certain other embodiments of the present disclosure. Compared to the embodiments depicted in FIGS. 1B to 5 where valve membrane 102 is depicted to have a flat portion 110, valve membrane 600 has a folded disc portion 111, comprising at least one ridge 602 and at least one groove 604. In certain configurations, ridge 602 and groove 604 extend circumferentially around the entirety of the folded flat portion 111 (360 degrees), to enable valve membrane 600 to stretch or deform evenly in all directions. In general, folded disc portion 111 may be circular, elliptical or may have another shape, as discussed previously with respect to flat portion 110. Valve membrane 600 further comprises conical portion 606 (functionally similar to conical portion 112) that tapers into a cylindrical tip 118 at the apex of the cone.

Still referring to FIG. 6, in operation, a valve comprising valve membrane 600 operates similarly to the valve embodiments described with respect to FIGS. 1B to 5. In the absence of an external force, valve membrane 600 is in an undeformed position, thereby allowing fluid to pass from a fluid inlet to a fluid outlet (not shown in FIG. 6) through a clearance between conical portion 112 and a valve seat similar to valve seat 104 (not shown in FIG. 6). When an external force is applied near region 608 in the direction of arrow 610, valve membrane 600 is pushed inwards (in the direction of arrow 610). The application of force at the center of folded flat portion 111 causes conical portion 112 to move downwards (in the direction of arrow 610) and further causes folded flat portion 111 to stretch radially. The stretching deformation of valve membrane 600 closes the separation between valve membrane 600 and the valve seat (not shown in FIG. 6). In the radially deformed position, the ridges and grooves of valve membrane 600 (e.g., elements 603, 604) will flatten out (or become shallower) and provide allowance for radial expansion of valve membrane 600.

Still referring to FIG. 6, in certain aspects, the total deformable surface of valve membrane 600 is more than that of a comparably sized valve membrane 102. In other words, valve membrane 600 is able to radially deform farther than a comparably sized valve membrane 102. Therefore, in valve designs supporting high flow rates, generally due to greater separation between conical portion 112 and beveled surface 234, valve membrane 600 may be considered a more suitable choice. In certain configurations, valve membrane 600 and valve membrane 102 are interchangeably usable with the same valve seat 104. In other words, no design changes are required to valve seat 104 to be able to operate with either of the valve membranes 102, 600.

In certain configurations, valve membrane 102 may comprise elastomeric material such as commercially available silicone having Shore A Durometer hardness in the range 30-60 (e.g., 40). In certain configurations, the material used for valve membrane 102 has an elasticity modulus of less than 1.50 MPa or 230 pounds per square inch (PSI). The elasticity modulus may for example be 200 PSI (1.20 MPa). In certain configurations, the valve membranes 102, 600 may be made from commercially available GE silicone LIM 6040 material.

Multi-channel fluid delivery systems may be used in certain medical applications to deliver multiple fluids simultaneously using multiple fluid channels. For example, a two-channel fluid delivery system comprises two fluid delivery channels that may operate independently of each other. In certain configurations, a single sheet of elastomeric material may be molded into multiple valve membranes that can be used to operate multiple valves in a multi-channel fluid delivery system. By way of illustration, and not limitation, the operation of a disposable portion comprising two input fluid delivery channels and one output fluid delivery channel is disclosed below.

Figure 7:
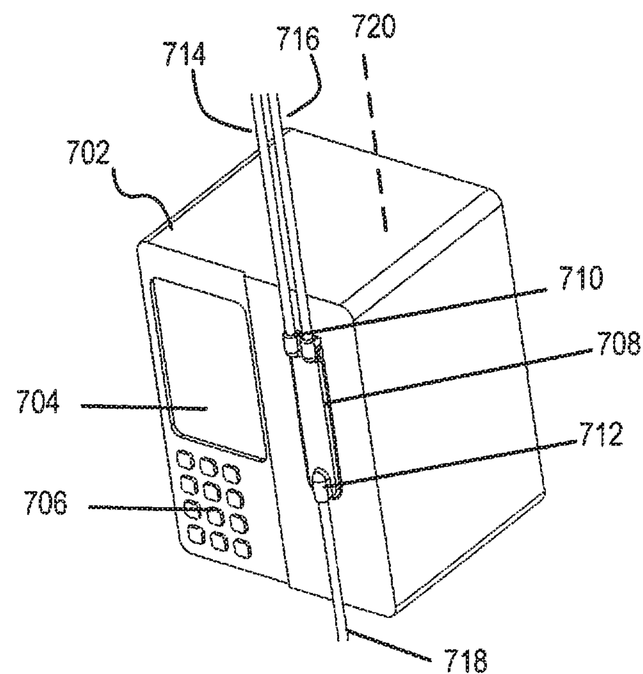
FIG. 7 is a diagrammatic view of a pump instrument and a disposable unit, in accordance with certain configurations of the present disclosure.

FIG. 7 is a diagrammatic view of fluid delivery pump 702 and disposable unit 708, in accordance with certain configurations of the present disclosure. Pump 702 comprises display screen 704 for displaying status information to a user and keyboard 706 to allow a user to input commands to pump 702. Pump 702 is fitted with a cassette or a disposable unit 708. In certain configurations, disposable unit 708 is positioned on the same panel as display screen 704 to allow easy access and continuous visibility of operation of disposable unit 708 to a user. Disposable unit 708 comprises two input fluid lines 714, 716 at input end 710 and a single fluid output line 718 coupled to output end 712. In operation, pump 702 controls delivery of fluid from input fluid lines 714, 716 to output fluid line 718. For example, pump 702 may control fluid delivery such that fluid in output fluid line 718 comes only from input fluid line 714 or only from input fluid line 716 or is a combination of fluids from fluid lines 714, 716. In certain configurations, pump 702 may mix fluids from input fluid lines 714, 716 in a pre-determined proportion by controlling the duration of opening and closing of input fluid lines 714, 716. Pump 702 may control fluid delivery using a valve configuration disclosed with respect to FIGS. 1-6 of the present disclosures.

Figure 8:
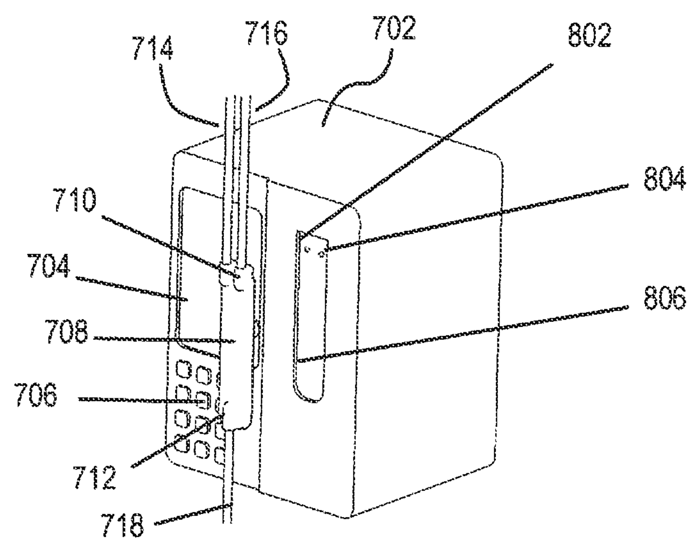
FIG. 8 is a diagrammatic view of a pump instrument and a disposable unit, in accordance with certain configurations of the present disclosure.

FIG. 8 is a diagrammatic view of pump 702 and disposable unit 708, in accordance with certain configurations of the present disclosure. Compared to the view depicted in FIG. 7 where disposable unit is attached to pump 702, disposable unit 708 in FIG. 8 is detached from pump 702. Detaching disposable unit 708 has exposed two valve activation mechanisms 802, 804 in area 806 of pump 702. In certain configurations, area 806 is recessed to allow a secure fit of disposable unit 708 during the operation of pump 702. In certain configurations, valve activation mechanisms 802, 804 are shaped as cylindrical or conical protrusions ("fingers") that can move back-and-forth in the body of disposable unit 708 to push a valve located within disposable unit 708 to cause the valve to close or open.

Figure 9:
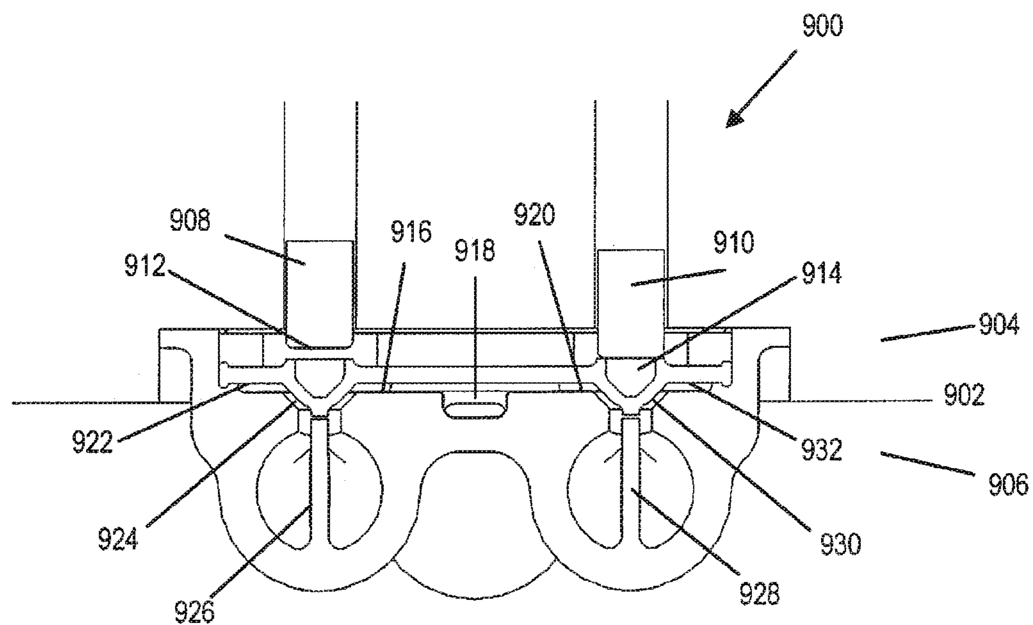
FIG. 9 is a diagrammatic cross-sectional view of a pump instrument and a disposable unit, in accordance with certain configurations of the present disclosure.

FIG. 9 is a diagrammatic cross-sectional view of pump instrument 702 and disposable unit 708, in accordance with certain configurations of the present disclosure. The cross-sectional view depicted in FIG. 9 is looking at pump 702 and disposable unit 708 in the direction of arrow 720 of FIG. 7. Line 902 marks the boundary between pump 702 on side 904 and disposable unit 708 on side 906. Pump 702 comprises two actuators 908, 910 for pushing against valve membranes 912 and 914. Openings 922 and 916 correspond to fluid inlet and outlet of a first valve controlling delivery of fluid from fluid line 714. Openings 932 and 920 correspond to fluid inlet and outlet for a second valve controlling fluid delivery from fluid line 716. Outputs 916 and 920 are fluidly connected to fluid channel 918 that extends to output end 712 of disposable unit 708. Bottom 926 of the valve seat of the first valve and bottom 928 of the second valve operate similar to bottom 230 described with respect to valve configurations depicted in FIGS. 1B to 6. Clearances 924 and 930 work similar to clearance 236 described with respect to FIG. 1B to 6. The configurations depicted in FIG. 9 illustrates valve membranes 912 and 914 made from a contiguous sheet of material. In certain aspects, using a single sheet may lend itself to economical and reliable manufacturing of valves.

Figure 10:
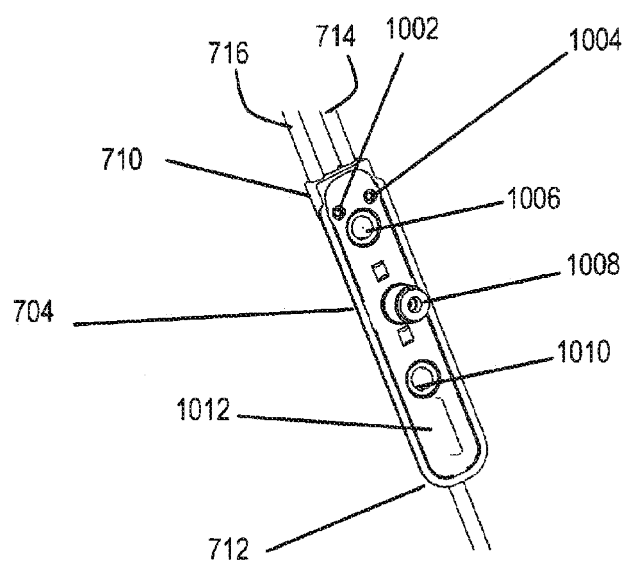
FIG. 10 is a diagrammatic view of a disposable unit, in accordance with certain configurations of the present disclosure.

FIG. 10 is a diagrammatic view of disposable unit 708, in accordance with certain configurations of the present disclosure. FIG. 10 depicts the backside of disposable unit 708. The backside faces pump 702 during fluid delivery operation. The backside includes openings 1002 and 1004 at input end 710. Openings 1002 and 1004 expose valve membranes of valves controlling fluid delivery through fluid channels comprising fluid inputs 716 and 714 respectively. During operation, external actuators located in pump 702 exert pushing force on valve membranes located inside openings 1002 and 1004 to open and close corresponding valves, as needed. Areas 1006 and 1010 depict membranes that interface with pressure sensors (not shown in FIG. 10) to give an indication of the upstream and the downstream fluid pressures. Locking mechanism 1008 is used to secure disposable unit 708 to pump 702.

It will be appreciated that various valve configurations described herein may be molded as a part of an intravenous (IV) infusion disposable unit. The various valve configurations may also be used in a pump mechanism or other fluid delivery systems. For example, valve configurations of the present disclosure may be used in a positive displacement pump wherein a first valve configuration is used on the intake side of the positive displacement pump and a second valve configuration is used on the fluid delivery side of the positive displacement pump. In certain aspects, a positive displacement pump comprising valve configurations of the present disclosure at the fluid intake and/or the fluid delivery side may be used to control the direction of fluid flow through the positive displacement pump.

It will further be appreciated that certain portions of the valve configurations of the present disclosure can be scaled up or down to provide a certain cross-sectional flow area, thereby controlling a flow rate through the valve. It will further be appreciated that a coefficient of resiliency of the valve membrane material may influence the choice of the mechanism providing the external force to deform the valve membrane and vice versa. For example, if a valve membrane comprises a material having a lower coefficient of resiliency, a relatively greater force may be required to cause radial deforming of the valve membrane. In such a case, a larger actuation area 114 may be provided and/or a higher power external electromechanical actuator may be used for operation of such a valve design. It will further be appreciated that the rate of fluid delivery through a valve configuration is affected by choice of various design parameters such as the physical dimensions of gap 228, clearance 236, and so on.

In certain aspects, configurations of the present disclosure provide a valve mechanism useful in a fluid delivery system to fluidly connect and disconnect a fluid inlet and a fluid outlet. In certain aspects, configurations of the present disclosure include a valve membrane fitted within a valve seat. The valve membrane comprises a conical portion and the valve seat comprises a corresponding beveled surface. During operation, when the valve is in the open position, the valve membrane is undeformed, allowing fluid to pass through a clearance between the conical portion and the beveled surface. An external force pushing at the base of the conical portion, in the direction of the conical portion, causes the valve membrane to deform in a radially outward direction, thereby closing the separation between the conical portion and the beveled surface (i.e., the valve is in the closed position). When the external force is removed, the valve membrane resiles back to the undeformed position, causing the valve to return to the open position, and again allowing passage of fluid from the fluid inlet to the fluid outlet. In certain aspects, valve mechanisms of the present disclosure offer the advantage that because the restorative energy for opening the valve is stored in the valve material itself, valves do not require other restorative parts such as a coil spring and therefore valves can be fabricated with fewer parts.

While the various embodiments described above refer to a conical protrusion on valve membrane 102 (or 111), in general, embodiments may use various other shapes. For example, in certain embodiments, a valve for controlling delivery of fluid between a fluid inlet and a fluid outlet, may comprise a first portion (e.g., valve seat 104) having a chamber fluidly connected to the fluid inlet and the fluid outlet and a second portion (e.g., valve membrane 102) having a protruding portion fitted within the chamber such that fluid can flow from the fluid inlet to the fluid outlet through the chamber around the protruding portion when the protruding portion is not deformed and fluid cannot flow from the fluid inlet to the fluid outlet through the chamber when the protruding portion is deformed to touch at least a portion of a wall of the chamber. The protruding portion may be conical, or may be shaped like a pyramid or an obelisk, or some other shape such that application of external force causes the protruding portion to deform and touch a portion of the wall of the chamber to cut off fluid transfer between the fluid inlet and the fluid outlet. As previously discussed, when the protruding portion is conically shaped, a corresponding beveled surface on the first portion can be used to cause such a closure under external force. In certain embodiments, the first portion comprises a rigid material and the second portion comprises an elastomeric material to allow the protruding portion to deform under force and resile when the force is taken away.

Although embodiments of the present disclosure have been described and illustrated in detail, it is to be clearly understood that the same is by way of illustration and example only and is not to be taken by way of limitation, the scope of the present invention being limited only by the terms of the appended claims.

What is claimed is:

1. A valve in a fluid delivery system, comprising:

a valve seat comprising a fluid inlet, a fluid outlet, a conical well having an opening with a beveled surface and a bottom, the bottom in a different plane than the beveled surface, and a flow path passing from the fluid inlet through the conical well of the valve seat to the fluid outlet; and a valve membrane comprising a conical portion having a central axis, a base, and a tip, the conical portion configured to fit within the conical well of the valve seat, the valve membrane configured to allow fluid to flow from the fluid inlet along the flow path, between the conical well and conical portion, to the fluid outlet when the conical portion is in an undeformed position, and block the flow path when in a radially deformed position;

wherein the valve seat and valve membrane are configured such that the conical portion is separated from the beveled surface by a clearance when the valve membrane is in the undeformed position, and the conical portion is fluidly sealed against the beveled surface in the radially deformed position, wherein engagement of the tip of the conical portion against the bottom of the conical well compresses the valve member axially and radially expands the conical portion to contact the beveled surface.

2. The valve of claim 1 wherein:

the valve seat comprises a rigid material; and the valve membrane comprises an elastomeric material.

3. The valve of claim 2, wherein the elastomeric material comprises silicone.

4. The valve of claim 1, wherein the valve membrane comprises a pushable portion such that pushing against the pushable portion by an external force puts the valve into the radially expanded position.

5. The valve of claim 1, wherein a disposable portion of an intravenous fluid pump comprises the valve.

6. The valve of claim 1, wherein a positive displacement pump comprises a first one of the valve on a fluid intake side and a second one of the valve on a fluid delivery side.

7. The valve of claim 1, further comprising a retaining cap, the retaining cap provided to fit over the valve seat to secure the valve membrane in place during operation of the valve.

8. A valve in a fluid delivery system, comprising:

a valve seat comprising a conical well having a conical surface and a bottom, the bottom in a different plane than the conical surface, the conical well positioned along a flow path that extends through the conical well from a fluid inlet of the valve seat to a fluid outlet of the valve seat, through the conical well, and to the fluid outlet; and a valve membrane comprising a central axis and a conical portion having a tip, the conical portion configured to be received within the conical well, the membrane having an unconstrained configuration and a deflected configuration wherein engagement of the tip of the conical portion against the bottom compresses the valve member axially and radially expands the conical portion in the deflected configuration;

wherein the conical portion is separated from the conical surface by a gap when the valve membrane is in the unconstrained configuration, such that fluid may be conducted through the conical well, and the conical portion contacts the conical surface when the membrane is in the deflected configuration, thereby blocking fluid flow from the fluid inlet to the fluid outlet.

9. The valve of claim 8, wherein:

the valve seat comprises a rigid material; and the valve membrane comprises an elastomeric material.

10. The valve of claim 9, wherein the elastomeric material comprises silicone.

11. The valve of claim 8, wherein the valve membrane comprises a pushable portion such that pushing against the pushable portion by an external force puts the valve membrane into the deflected configuration.

12. The valve of claim 8, wherein the conical portion is separated from all surfaces of the conical well by a clearance when the valve membrane is in the unconstrained configuration, and the conical portion touches the conical well when the valve membrane is in the deflected configuration.

* * * * *